US00PP27975P3

(12) United States Plant Patent
Misato

(10) Patent No.: US PP27,975 P3
(45) Date of Patent: May 2, 2017

(54) *SENECIO* PLANT NAMED 'SUNSENEGOROKU'

(50) Latin Name: *Senecio cruentus*
Varietal Denomination: Sunsenegoroku

(71) Applicant: Tomoya Misato, Shiga (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 8 days.

(21) Appl. No.: 14/756,530

(22) Filed: Sep. 15, 2015

(65) Prior Publication Data

US 2017/0079186 P1 Mar. 16, 2017

(51) Int. Cl.
*A01H 5/02* (2006.01)

(52) U.S. Cl.
USPC ..... Plt./480

(58) Field of Classification Search
USPC ..... Plt./480
See application file for complete search history.

*Primary Examiner* — June Hwu
(74) *Attorney, Agent, or Firm* — C. A. Whealy

(57) ABSTRACT

A new and distinct cultivar of *Senecio* plant named 'Sunsenegoroku', characterized by its upright and uniformly mounded plant habit; vigorous growth habit; freely branching habit; freely flowering habit; and daisy-type inflorescences with ray florets that are violet blue in color towards the apex and pale pink in color towards the base.

1 Drawing Sheet

Botanical designation: *Senecio cruentus.*
Cultivar denomination: 'SUNSENEGOROKU'.

BACKGROUND OF THE INVENTION

The present invention relates to a new and distinct cultivar of *Senecio* plant, botanically known as *Senecio cruentus*, and hereinafter referred to by the name 'Sunsenegoroku'.

The new *Senecio* plant is a product of a planned breeding program conducted by the Inventor in Higashiomi, Shiga, Japan. The objective of the breeding program is to create new upright and uniformly mounding *Senecio* plants with a freely-branching habit and numerous attractive inflorescences.

The new *Senecio* plant originated from a cross pollination conducted by the Inventor in March, 2010 of a proprietary selection of *Senecio cruentus* identified as code number 09-25, not patented, as the female, or seed, parent with a proprietary selection of *Senecio cruentus* identified as code number 09-81, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2011.

Asexual reproduction of the new *Senecio* plant by terminal cuttings in a controlled greenhouse environment in Higashiomi, Shiga, Japan since October, 2011 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunsenegoroku'. These characteristics in combination distinguish 'Sunsenegoroku' as a new and distinct *Senecio* plant:

1. Upright and uniformly mounded plant habit.
2. Vigorous growth habit.
3. Freely branching habit.
4. Freely flowering habit.
5. Daisy-type inflorescences with ray florets that are violet blue in color towards the apex and pale pink in color towards the base.

Plants of the new *Senecio* can be compared to plants of the female parent selection. Plants of the new *Senecio* differ from plants of the female parent selection in the following characteristics:

1. Plants of the new *Senecio* are more freely branching than plants of the female parent selection.
2. Plants of the new *Senecio* and the female parent selection differ in ray floret color as plants of the female parent selection have white-colored ray florets.

Plants of the new *Senecio* can be compared to plants of the male parent selection. Plants of the new *Senecio* differ from plants of the male parent selection in the following characteristics:

1. Plants of the new *Senecio* are more freely branching than plants of the male parent selection.
2. Plants of the new *Senecio* and the male parent selection differ in ray floret color as plants of the male parent selection have ray florets that are light blue in color towards the apex and light pink in color towards the base.

Plants of the new *Senecio* can also be compared to plants of *Senecio cruentus* 'Sunsenebu', disclosed in U.S. Plant Pat. No. 12,104. In side-by-side comparisons conducted in Higashiomi, Shiga, Japan, plants of the new *Senecio* differed from plants of 'Sunsenebu' in the following characteristics:

1. Plants of the new *Senecio* were taller and more upright than plants of 'Sunsenebu'.

2. Plants of the new *Senecio* had thicker and darker green-colored stems than plants of 'Sunsenebu'.
3. Plants of the new *Senecio* had smaller and darker green-colored leaves than plants of 'Sunsenebu'.
4. Plants of the new *Senecio* had smaller inflorescences than plants of 'Sunsenebu'.
5. Plants of the new *Senecio* and 'Sunsenebu' differed in ray floret color as plants of 'Sunsenebu' had violet-colored ray florets.
6. Plants of the new *Senecio* had shorter peduncles than plants of 'Sunsenebu'.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet is a side perspective view of a typical flowering plant of 'Sunsenegoroku' grown in a container.

The photograph at the bottom of the sheet is a close-up view of a typical flowering plant of 'Sunsenegoroku'.

DETAILED BOTANICAL DESCRIPTION

The aforementioned photographs, following observations and measurements describe plants grown during the winter in 15-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Senecio cruentus* 'Sunsenegoroku'.

Parentage:

*Female, or seed, parent*.—Proprietary selection of *Senecio cruentus* identified as code number 09-25, not patented.

*Male, or pollen, parent*.—Proprietary selection of *Senecio cruentus* identified as code number 09-81, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching.

Plant description:

*Plant form and growth habit*.—Upright and uniformly mounded plant habit; daisy-type inflorescences positioned above the foliar plane; freely branching habit; vigorous growth habit; freely branching habit with about eight primary lateral branches with numerous secondary branches.

*Plant height*.—About 39 cm.

*Plant diameter*.—About 34.5 cm.

*Lateral branches*.—Length: About 29 cm. Diameter: About 7.4 mm. Internode length: About 7.8 cm. Strength: Strong. Aspect: Upright to outwardly. Texture: Moderately pubescent. Color: Close to 146B.

*Leaf description*.—Arrangement: Alternate, simple. Length: About 6.5 cm. Width: About 7 cm. Shape: Cordate. Apex: Acute. Base: Cordate. Margin: Crenate and serrate, shallow lobes; slightly undulate. Texture, upper surface: Sparsely pubescent; rough. Texture, lower surface: Moderately pubescent; rough. Luster, upper and lower surfaces: Matte. Venation pattern: Pinnate; reticulate. Color: Developing leaves, upper surface: Close to 137C. Developing leaves, lower surface: Close to 138B. Fully expanded leaves, upper surface: Close to 146A; venation, close to 146C. Fully expanded leaves, lower surface: Close to 147B; venation, close to 146D. Leaf petioles: Length: About 5.2 cm. Diameter: About 2.2 mm. Texture, upper and lower surfaces: Sparsely pubescent. Color, upper and lower surfaces: Close to 146C.

Inflorescence description:

*Appearance*.—Daisy-type inflorescences with narrowly elliptic-shaped ray florets; inflorescences arising from upper leaf axils and positioned above the foliar plane on strong peduncles; disc and ray florets developing acropetally on a capitulum; inflorescences face mostly upright to slightly outwardly; freely flowering habit with about 46 inflorescences developing per plant.

*Fragrance*.—None detected.

*Natural flowering season*.—Plants of the new *Senecio* begin flowering about 22 weeks after planting; plants flower continuously from winter to late spring in Japan.

*Inflorescence buds*.—Height: About 1.3 cm. Diameter: About 6.1 mm. Shape: Globose. Color: Close to 76B.

*Inflorescence size*.—Diameter: About 5.1 cm. Depth (height): About 2.15 cm. Disc diameter: About 1 cm.

*Receptacles*.—Diameter: About 6.1 mm. Height: About 1.4 mm. Color: Close to N144D.

*Ray florets*.—Length: About 2.28 cm. Width: About 6.4 mm. Shape: Elliptic. Apex: Acute to rounded. Base: Acute. Margin: Entire. Aspect: Initially upright, then horizontal; flat. Texture, upper and lower surfaces: Smooth, glabrous. Number of ray florets per inflorescence: About 13 in a single whorl. Color: When opening, upper surface: Towards the apex, close to N88A; towards the base, close to 76C. When opening, lower surface: Close to 91D. Fully opened, upper surface: Towards the apex, close to 93B; mid-section, close to 91B; towards the base, close to 76D; with development, distal color becoming closer to N89C and proximal color becoming closer to 91D. Fully opened, lower surface: Close to 84D.

*Disc florets*.—Shape: Tubular; apex dentate, five-pointed. Length: About 7.6 mm. Diameter, at apex: About 1.3 mm. Number of disc floret per inflorescence: About 130. Color, immature: Close to 79A. Color, mature: Close to 83A.

*Phyllaries*.—Quantity per inflorescence: About 13 in a single whorl. Length: About 1.7 mm. Width: About 1.3 mm. Shape: Lanceolate. Apex: Narrowly acute. Base: Fused. Margin: Entire. Texture, upper and lower surfaces: Smooth, glabrous. Color, upper surface: Close to 138B. Color, lower surface: Close to 138A; towards the apex, close to 138C tinged with close to 79B.

*Peduncles*.—Length: About 4.3 cm. Diameter: About 1.2 mm. Strength: Strong. Aspect: Upright to outwardly. Texture: Pubescent. Color: Close to 144A.

*Reproductive organs*.—Androecium: Present on disc florets only. Filament length: About 1.5 mm. Filament color: Close to 4D. Anther size: About 1.5 mm by 0.5 mm. Anther shape: Ellipsoidal. Anther color: Close to 92C. Pollen amount: Moderate. Pollen color: Close to 6B. Gynoecium: Present on both ray and disc florets. Pistil length: About 6.5 mm. Stigma shape: Bi-parted. Stigma color: Close to N92A. Style color: Close to 145C. Ovary color: Close to 145C.

*Seeds and fruits*.—Seed and fruit development have not been observed on plants of the new *Senecio*.

Disease & pest resistance: Plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sunsenegoroku' as illustrated and described.

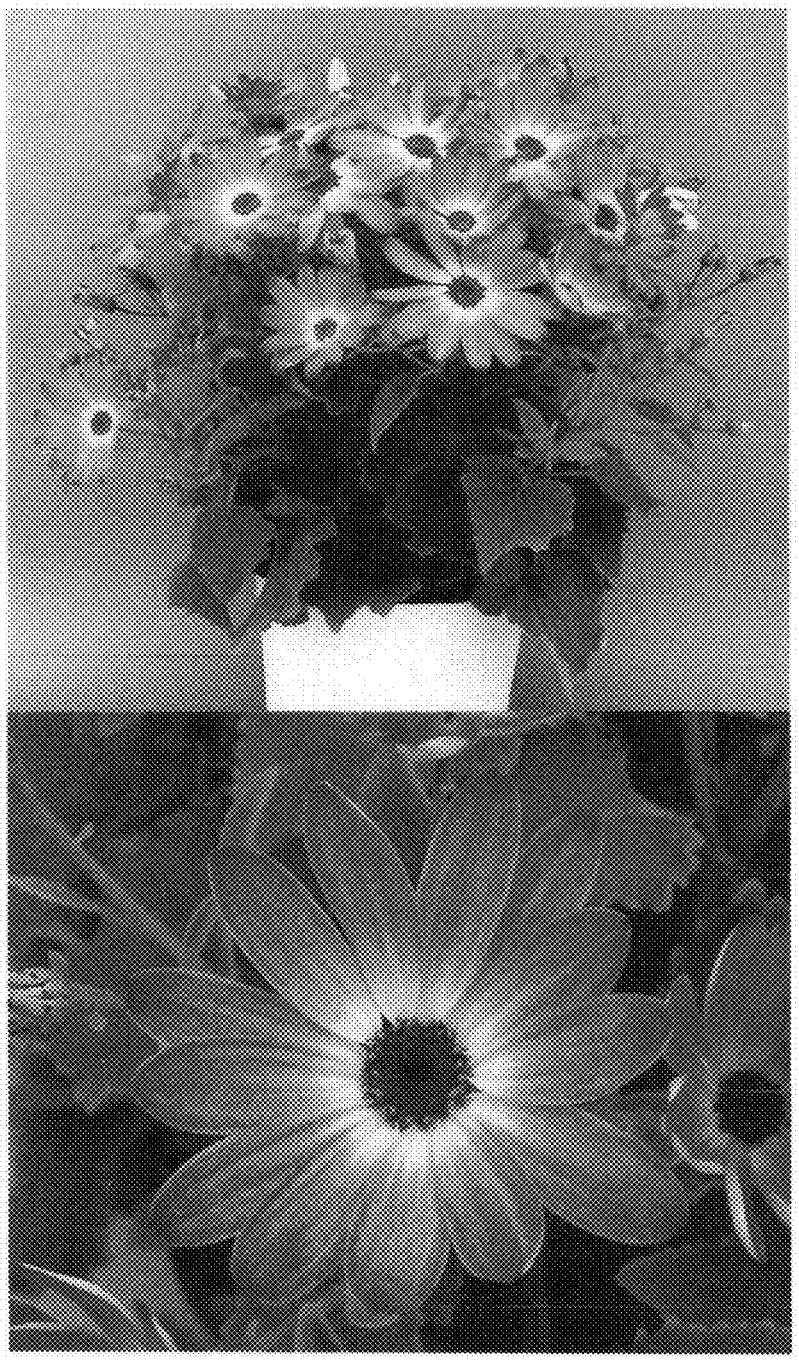

* * * * *